United States Patent [19]

Massardo et al.

[11] Patent Number: 4,980,376
[45] Date of Patent: Dec. 25, 1990

[54] BENZOYL-UREAS HAVING INSECTICIDE ACTIVITY

[75] Inventors: Pietro Massardo; Paolo Piccardi, both of Milan; Franco Rama, Busto Arsizio; Vincenzo Caprioli, S. Martino Siccomario, all of Italy

[73] Assignee: Istituto Guido Donegani S.p.A., Milan, Italy

[21] Appl. No.: 540,464

[22] Filed: Jun. 19, 1990

Related U.S. Application Data

[63] Continuation of Ser. No. 405,588, Sep. 11, 1989, abandoned, which is a continuation of Ser. No. 296,889, Jan. 12, 1989, abandoned, which is a continuation of Ser. No. 185,373, Apr. 21, 1988, abandoned, which is a continuation of Ser. No. 71,583, Jul. 9, 1987, abandoned, which is a continuation of Ser. No. 868,010, May 29, 1986, abandoned.

[30] Foreign Application Priority Data

May 30, 1985 [IT] Italy ............................... 20973 A/85

[51] Int. Cl.$^5$ ..................... C07C 275/54; A01N 47/34
[52] U.S. Cl. ........................................ 514/594; 564/44
[58] Field of Search ................... 564/44, 23; 514/594, 514/584

[56] References Cited

U.S. PATENT DOCUMENTS 3,933,908  1/1976  Wellinga et al. ...................... 564/44

FOREIGN PATENT DOCUMENTS

| 3235419 | 4/1983 | Fed. Rep. of Germany | 564/44 |
| 212463 | 12/1984 | Japan | 564/44 |
| 237056 | 11/1985 | Japan | 564/44 |

*Primary Examiner*—Carolyn S. Elmore
*Attorney, Agent, or Firm*—Stevens, Davis, Miller & Mosher

[57] ABSTRACT

Compounds are disclosed having formula:

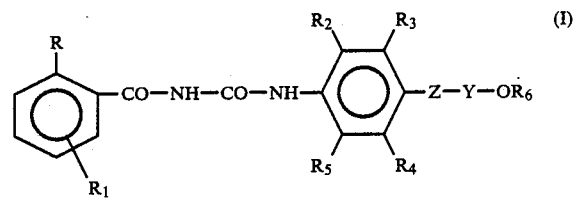

wherein:

R is Cl, F;

$R_1$ is H, Cl, F;

$R_2$ and $R_5$, equal to or differing from each other, are H, halogen, alkyl $C_1$–$C_4$;

$R_3$ and $R_4$, equal to or differing from each other, are: H, halogen, alkyl, haloalkyl, alkoxy, haloalkoxy, alkenyl, haloalkenyl, alkenyloxy, haloalkenyloxy or alkynyl;

Z is O, S or a group $NR_7$, wherein $R_7$ is alkyl $C_1$–$C_3$ or H;

Y is alkylene $C_2$–$C_4$, haloethylene or haloethenyl;

$R_6$ is alkyl $C_1$–$C_4$, haloalkyl $C_1$–$C_4$, alkenyl $C_3$–$C_4$, haloalkenyl $C_3$–$C_4$, cycloalkyl $C_3$–$C_4$, halocycloalkyl $C_3$–$C_4$ or cycloalkenyl $C_3$–$C_4$.

The compounds having formula (I) are endowed with an elevated insecticide activity, which shows itself chiefly against insect larvae and eggs.

9 Claims, No Drawings

4,980,376

BENZOYL-UREAS HAVING INSECTICIDE ACTIVITY

This application is a Continuation of application Ser. No. 405,588, filed Sept. 11, 1989 which in turn is a continuation of Ser. No. 296,889, filed Jan. 12, 1989 which in turn is a Continuation of application Ser. No. 185,373, filed Apr. 21, 1988 which in turn is a Continuation of application Ser. No. 071,583, filed July 9, 1987, which in turn is a Continuation of application Ser. No. 868,010, filed May 29, 1986 all abandoned.

BACKGROUND OF THE INVENTION

The present invention relates to benzoylurea derivatives having insecticide activity and, more precisely, relates to 1-benzoyl-3-aryl-urea derivatives which are particularly active against insect larvae and eggs, noxious in agrarian and civil fields and in the use of such derivatives. Furthermore, the invention relates to the process of synthesis of these ureas.

Several 1-benzoyl-3-aryl-urea derivatives, endowed with insecticide activity, are known.

Among them is Diflubenzuron, usual name of the compound 1-(2,6-difluorobenzoyl)-3-(4-chlorophenyl)-urea, disclosed in U.S. Pat. No. 3,933,908.

Diflubenzuron, however, is suspected of being a carcinogen [European Chem. News 6 (16), 29 (1978)], as it contains the unit of 4-chloro-aniline in the molecule.

THE PRESENT INVENTION

We have now found new insecticidal 1-benzoyl-3-arylurea derivatives, which form the object of the present invention, and have the general formula:

(I) [structure: benzene ring with R, $R_1$ substituents, —CO—NH—CO—NH— linked to second benzene ring with $R_2$, $R_3$, $R_4$, $R_5$ substituents and —Z—Y—$OR_6$]

wherein:
R represents a chlorine or fluorine atom;
$R_1$ represents a hydrogen, chlorine or fluorine atom;
$R_2$ and $R_5$, equal to or differing from each other, represent hydrogen, a halogen atom, an alkyl group containing from 1 to 4 carbon atoms;
$R_3$ and $R_4$, equal to or differing from each other, represent hydrogen, a halogen atom, an alkyl, haloalkyl, alkoxy, haloalkoxy, alkenyl, haloalkenyl, alkenyloxy, haloalkenyloxy or alkynyl group;
Z represents an oxygen atom, a sulphur atom or a group $NR_7$, wherein $R_7$ is an alkyl $C_1$–$C_3$ or H;
Y represents an alkylene group containing from 2 to 4 carbon atoms, a haloethylene or a haloethenyl group;
$R_6$ represents an alkyl $C_1$–$C_4$, haloalkyl $C_1$–$C_4$, alkenyl $C_3$–$C_4$, haloalkenyl $C_3$–$C_4$, cycloalkyl $C_3$–$C_4$, halocycloalkyl $C_3$–$C_4$ or cycloalkenyl $C_3$–$C_4$ group.

In the aforesaid definitions, by the term "halogen" is meant, preferably, a fluorine, chlorine or bromine atom.

The compounds having formula (I) have a high insecticide activity and are fit for use in agrarian, forestal, civil and veterinary fields, in the fight against insect infestations.

In the specification of the preparation of the compounds having formula (I) reported hereinafter, symbols R, $R_1$, $R_2$, $R_3$, $R_4$, $R_5$, $R_6$, Z and Y have the same meanings as in formula (I) unless otherwise specified.

The compounds having formula (I) are obtained by reaction between a benzoyl-isocyanate having formula:

(II) [structure: benzene ring with R, $R_1$ substituents, —CO—N=C=O]

with an aromatic amine having formula:

(III) [structure: $H_2N$— benzene ring with $R_2$, $R_3$, $R_4$, $R_5$ substituents —Z—Y—$OR_6$]

The reaction does not require the presence of catalysts and is carried out in an inert solvent, at a temperature ranging between 0° C. and the boiling temperature of the mixture.

Aromatic hydrocarbons, chlorinated hydrocarbons, ethers, ketones, and acetonitrile are suitable solvents The benzoyl-isocyanates having formula (II) are known compounds. In some cases they may be found on the market.

Amines having formula (III) may require a specific preparation. In particular, amines having formula (III) may be prepared according to known methods, for instance:

(a) the reaction of a sodium or potassium salt of a suitable amino-phenol (V), in dipolar aprotic solvents, with compound $CF_2$=CF—$OR_6$ (IV) wherein $R_6$ has the same meaning as in formula (I), at a temperature ranging between 0° C. and the room temperature, according to the following equation:

[structure (V): $H_2N$— benzene ring with $R_2$, $R_3$, $R_4$, $R_5$ —$O^-Na^+$] + $CF_2$=CF—$OR_6$ (IV) $\longrightarrow$

[structure (III): $H_2N$— benzene ring with $R_2$, $R_3$, $R_4$, $R_5$ —$OCF_2$—$CFHOR_6$]

(b) reduction, according to known techniques, of nitroderivatives having formula:

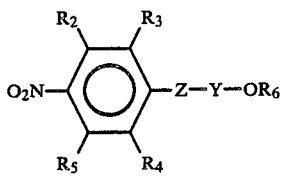  (VI)

In turn, the nitroderivatives having formula (VI) may be prepared, according to traditional techniques, for instance those wherein Y is haloethylene, by reacting a suitable 4-nitrophenyl or 4-nitrothiophenol sodium or potassium salt having formula (VII) with the compound having formula (IV), in suitable dipolar aprotic solvents, according to the equation:

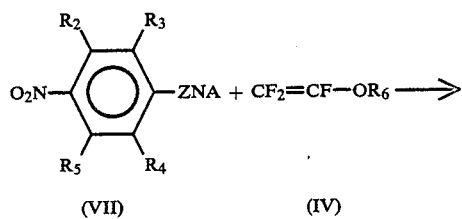

(VII)            (IV)

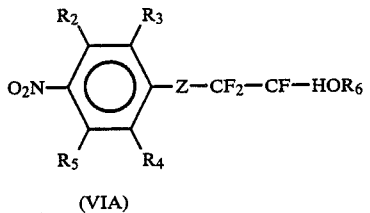

(VIA)

Those wherein Z is $=NR_7$ and Y is alkenyl, for instance, may be prepared by reacting the sodium salt of a suitable 4-nitro-N-(hydroxy-alkyl)aniline with tetrafluoroethylene, according to the equation:

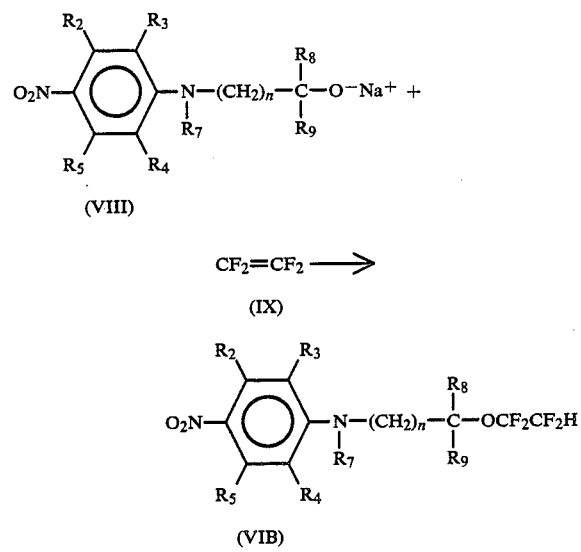

wherein $R_8$ and $R_9$ represent a hydrogen atom or an alkyl $C_1$-$C_3$ and n is an integer from 0 to 3.

The ethers having formula (IV) may be prepared according to the known method specified, for instance, in J. Am. Chem. Soc., 82, 5116 (1960) when $R_6$ is alkyl or aryl and in J. Org. Chem., 48, 242 (1983) when $R_6$ is polyhaloalkyl.

As will be apparent to the skilled technician, different alternative procedures may be used for the synthesis of the intermediates, and of the products having formula (I).

An alternative procedure for the synthesis of the compounds having formula (I) consists, for instance, in reacting a benzamide having formula:

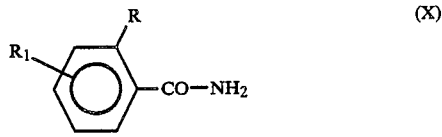  (X)

with an isocyanate having formula:

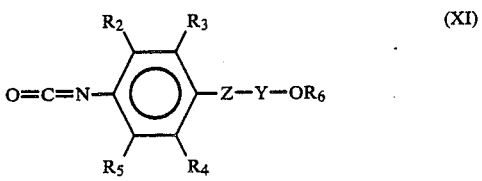  (XI)

Such reaction is carried out under conditions similar to those specified hereinabove for the reaction between the benzoyl-isocyanate having formula (II) and the amine having formula (III).

The preparation of the isocyanates having formula (XI) foresees, however, the preparation of amines having formula (III) and their reaction with phosgene. This aspect, together with the consideration that the benzoyl-isocyanates having formula (II) are available as much as the amides having formula (X) are available, leads to the general preference for the synthesis method mentioned hereinbefore, namely, the reaction between the compounds having formulae (II) and (III).

As above mentioned, the compounds having formula (I) are endowed with a high insecticide activity which shows chiefly against insect larvae and eggs. Among these, those belonging to the Lepidoptera, Dipthera and Coleoptera orders, may be particularly fought by means of the compounds having formula (I).

These orders comprise a great many species, important for their noxiousness in the agrarian, forestal, civil and veterinary fields. Therefore, the compounds having formula (I) are fit for various uses, namely, for instance, the defense of agricultural cultivations against phytophagous insect infestations, the protection of environments against mosquitoes and flies, the protection of breeding-cattle against some cattle parasites, etc.

Furthermore, the compounds having formula (I) show a collateral acaricide activity.

For practical uses, the compounds having general formula (I) may be utilized as such or, more conveniently, in the form of compositions containing, in addition to one or more of the compounds having formula (I) as active constituent, inert solid or liquid carriers and, optionally, other conventional additives. According to the usual formulating practice, the compositions may be in the form of wettable powders, emulsifiable concentrates, etc.

The amount of active constituent in the compositions varies within wide ranges (1-95% by weight) depending on the type of composition and the use for which such composition is intended.

Whatever particular situations so require, or, in order to enlarge the action spectrum, other active substances such as, for instance, other insecticides or acaricides, may be added to the compositions.

The amount of active substances [compound having formula (I)] to be distributed for the insecticide treatment, depends on various factors such as, for instance, the type and degree of infestation, the environment in which infestation is had (agrarian cultivation, basins or water-courses, organic substrata of varied nature), the type of composition employed, climatic and environmental factors, available application means, etc. Generally, amounts of active substances ranging between 0.01 and 1 kg/ha are sufficient for a good disinfestation.

The following examples are given in order to better illustrate the invention and are not intended to be limiting.

The abbreviations which follow are used in the spectra of nuclear magnetic resonance of the proton ($^1$H-NMR) and of fluorine ($^{19}$F-NMR), reported in the examples:

s=singlet;
m=multiplet or unresolved complex signal;
d=doublet;
t=triplet;
b=(broad)=broad signal;
ABq=quartet of AB type.

EXAMPLE 1

Preparation of N-2,6-difluorobenzoyl-N'-3,5-dichloro-4[1,1,2-trifluoro-2-(perfluoroethoxy)ethoxy]-phenylurea (compound No. 1).

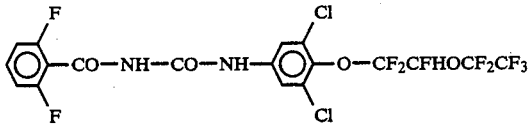

1.0 g of 3,5 dichloro-4-[1,1,2-trifluoro-2-(perfluoroethoxy)ethoxy]aniline (as per Example 3 below), dissolved in 10 ml. of anhydrous ether, are introduced into a flask having a 50 ml capacity and equipped with cooler, dropping funnel and magnetic stirrer. Then, 0.7 g of 2,6-difluorobenzoylisocyanate, suspended in 10 ml of anhydrous tetrahydrofuran, are dripped in at room temperature. The mixture is kept under stirring for 60 minutes, then cooled and filtered. The precipitate is concentrated under reduced pressure and the product is separated by filtering. 1.28 g of the benzoylurea having a melting point of 128°-130° C. is obtained.

EXAMPLE 2

Starting from the anilines specified in Example 3 below and operating under conditions similar to those specified in Example 1, the following compounds have been prepared, using 2,6-difluorobenzoylisocyanate:
Compound No. 2: N-2,6-difluorobenzoyl-N'-3,5-dichloro-4[1,1,2-trifluoro-2-(trifluoromethoxy)ethoxy]-phenylurea

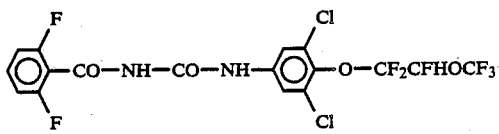

m.p.=108°-110° C.
Compound No. 3: N-2,6-difluorobenzoyl-N'-4-[1,1,2-trifluoro-2-(perfluoroethoxy)ethoxy]phenylurea

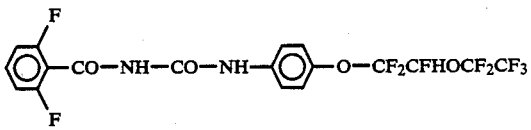

m.p.=153°-155° C.

When using the 2-chlorobenzoylisocyanate, the following compounds have been prepared:
Compound No. 4: N-2-chlorobenzoyl-N'-3,5-dichloro-4-[1,1,2-trifluoro-2-(perfluoroethoxy)ethoxy]-phenylurea

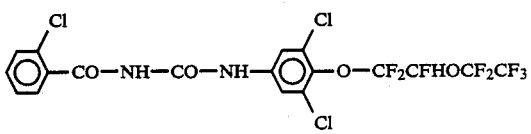

m.p.=109°-110° C.
Compound No. 5: N-2-chlorobenzoyl-N'-3,5-dichloro-4-[1,1,2-trifluoro-2-(trifluoromethoxy)ethoxy]-phenylurea

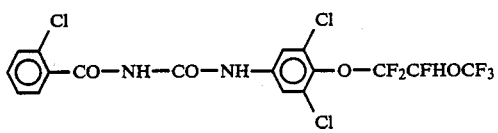

m.p.=138°-140° C.
Compound No. 6: N-2-chlorobenzoyl-N'-4-[1,1,2-trifluoro-2-(perfluoroethoxy)ethox]phenylurea

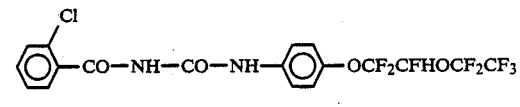

m.p.=120°-122°

EXAMPLE 3

Preparation of the intermediate anilines 32.5 millimoles of 2,6-dichloro-4-aminophenol, dissolved in 20 ml of anhydrous dioxane, are introduced, under nitrogen, into a 2-necked flask having a 50 ml capacity and equipped with cooler, magnetic stirrer and thermometer.

At room temperature, 8.12 millimoles of metallic sodium (or hydrosodium) are added, and stirring is effected at room temperature until the sodium salt is formed Under nitrogen atmosphere, the mass is transferred into a second 3-necked flask having a 100 ml capacity, and equipped with ethanol dried-ice cooler and magnetic stirrer, and dilution is effected with 20 ml of anhydrous DMF. Cooling is effected at −30° C., and 32.5 millimoles of the suitable vinylalkylether (IV), in a single portion and without solvents, are added. The mass is left overnight to return to room temperature while stirring.

Finally, the mass is poured into a solution of 10% soda, extracted with ethyl ether and purified for column chromatography, the unconverted phenol is recovered.

Using $CF_2=CF—OCF_2CF_3$ such as vinylether, 4 g of 3,5-dichloro-4-[1,1,2-trifluoro-2-(perfluoroethoxy)ethoxy]aniline, have been obtained with a conversion of 30% $^1$H-NMR 6.6 (s, 2H, arom.); 6.4–5.8 (dt, 1H, —CHF—); 3.8 (sb, 2H, NH$_2$); $^{19}$F—NMR—89.5–90.9 (ABq, 2F, —OCF—$_2$—CHF); —91.05 (s, 3F, CF$_3$); —93.6–96.12 (ABq, 2F, —OCF—$_2$CF$_3$; —148.75–149 (dt, 1F, —CF$_2$—CHF—)

Using $CF_2=CF—OCF_3$ such as vinylether, 5 g of 3,5-dichloro-4-[1,1,2-(trifluoromethoxy)ethoxy]aniline, has been obtained, with a conversion of 46%. $^1$H-NMR: 6.65 (s, 2H, arom); 6.15–5.95 (dt, $^1$H, —CHF—); 4.2 (sb, 2H, NH$_2$) $^{19}$F-NMR: −64.7 (s, 3F, —CF$_3$); −90.45 (m, 2F, —CF$_2$—); −149.5 (dm, 1F, —CHF)

By operating under conditions similar to those described hereinbefore, but using the 4-aminophenol and $CF_2=CFOCF_2CF_3$ such as vinylether, 8 g of 4-[1,1,2-trifluoro-2-(perfluoroethoxy)ethoxy]aniline, have been obtained with a conversion of 71% $^1$H-NMR: 6.95–6.55 (dd, 4H, arom.); 6.15–5.9 (dt. 1H, —CFH—); 3.7 (s, 2H, —NH ); $^{19}$F-NMR: −91.,8 (s, 3F, CF$_3$); −149.6 (dm, 1F, —CHF—); −94.4–96.3 (ABq, 2F, —OCF—$_2$—CFH—); −91.5–91.9 (ABq, 2F, —OCF—$_2$CF$_3$).

EXAMPLE 4

Testing of the insecticide activity.

Test 1

Residual immediate activity on larvae of *Spodoptera littoralis* (Lepidoptera).

Tobacco leaves were treated by mechanical spraying with a water-acetone solution of the product under examination, having an acetone content of 10% by volume and containing a surfactant.

After complete evaporation of the solvents, the leaves were infested with second-age larvae of Lepidoptera. The infested leaves were kept in a suitably conditioned environment during the test.

Likewise, tobacco leaves were infested and kept, after having been treated only with a water-acetone solution containing 10% of acetone and the surfactant, to be used as reference (comparison treatment).

Ten days after the infestation, and after having renewed the treated substratum at least once, a computation was made of the dead larvae with respect to the comparison treatment.

Test 2

Activity on larvae of *Aedes aegypti* (Diptera).

Spring water (297 ml.) was mixed with an acetonic solution (3 ml.) of the product under examination in a suitable concentration. 25 Dipter larvae, being 4 days of age, suitably fed, were introduced into the obtained solution. Other larvae were introduced for comparison purposes into a water-acetone solution (3 ml. acetone, 197 ml. of spring water) without any active product. Every 2–3 days, note was taken of the dead larvae and pupae and of the adults normally emerged from the cocoon, till the emergence from the cocoon of the insects in the comparison solution was over. The activity of the product under examination was expressed as a percent ratio of dead individuals, compared with the total number of treated individuals. The insecticide activity in the above-mentioned tests was expressed according to the following scale of values.

5 = complete activity (98–100% dead)
4 = high activity (80–97% dead)
3 = fair activity (60–79% dead)
2 = sufficient activity (40–59% dead)
1 = poor activity (20–39% dead)
0 = negligible or of no value activity (0–19% dead)

In the following Table 1, the insecticide activity data in the stated doses are reported, expressed in terms of the above scale of values.

TABLE 1

| | Insecticide Activity | | |
|---|---|---|---|
| | Test 1 | | Test 2 |
| Compound No. | Dose: 0.001% | Dose: 0.0005% | Dose: 0.01 ppm |
| 1 | 5 | 5 | 5 |
| 2 | 5 | 5 | 5 |
| 3 | 5 | 5 | 5 |
| 4 | 5 | 5 | 5 |
| 5 | 5 | 5 | 5 |
| 6 | 5 | 5 | 5 |
| Reference* | 4 | 3 | 5 |

(*) The following compound was taken as reference 1-(2,6-difluorobenzoyl)-3-(4-chlorophenyl)urea having formula:

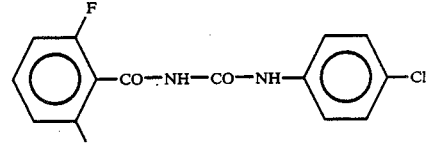

disclosed in U.S. Pat. No. 3,933,908.

We claim:

1. A compound having the formula:

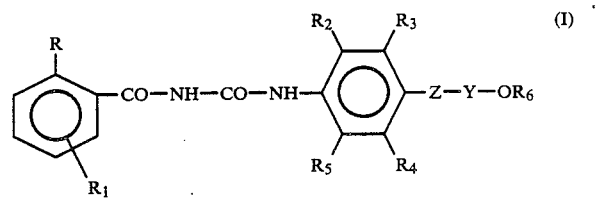

wherein: R represents a chlorine or fluorine atom;
R$_1$ represents a hydrogen, chlorine, or fluorine atom;
R$_2$ and R$_5$, equal to or differing from each other, represent a hydrogen atom or, a halogen atom;
R$_3$ and R$_4$, equal to or differing from each other, represent a hydrogen atom or, a halogen atom;
Z represents an oxygen atom;
Y represents an alkylene group containing from 2 to 4 carbon atoms, a haloethylene group; and
R$_6$ represents haloalkyl C$_1$–C$_4$.

2. A compound according to claim 1, and which is N-2,6-difluorobenzoyl-N'-3,5-dichloro-4-[1,1,2-trifluoro-2-(perfluoroethoxy)ethoxy]phenylurea.

3. A compound according to claim 1, and which is N-2,6-difluorobenzoyl-N'-3,5-dichloro-4-[1,1,2-trifluoro-2-(trifluoromethoxy)ethoxy]phenylurea.

4. A compound according to claim 1, and which is N-2,6-difluorobenzoyl-N'-4-[1,1,2-trifluoro-2-(perfluoroethoxy)ethoxy]phenylurea.

5. A Compound according to claim 1, and which is N-2-chlorobenzoyl-N'-3,5-dichloro-4-[1,2-trifluoro-2-(perfluoroethoxy)ethoxy]phenylurea.

6. A compound according to claim 1, and which is N-2-chlorobenzoyl-N'-3,5-dichloro-4-[1,1,2-trifluoro-2-(trifluoromethoy)ethoxy]phenylurea.

7. A compound according to claim 1, and which is N-2-chlorobenzoyl-N'-4[1,1,2-trifluoro-2-(perfluoroethoxy)ethoxy]phenylurea.

8. A method for combatting infestations of noxious insects consisting in distributing, in the infestation zone, an effective amount of at least one compound according to claim 1.

9. The method of claim 8, in which the said compound is in a composition also containing other adjuvants normally used in insecticidal compositions.

* * * * *

UNITED STATES PATENT AND TRADEMARK OFFICE
CERTIFICATE OF CORRECTION

PATENT NO.  : 4,980,376

DATED       : December 25, 1990

INVENTOR(S) : MASSARDO et al.

It is certified that error appears in the above-identified patent and that said Letters Patent is hereby corrected as shown below:

Column 7, line 14, change "-OCF—$_2$—CHF" to -- -OCF$_2$—CHF- --;

line 15, change "-OCF—$_2$CF$_3$;" to -- -OCF$_2$—CF$_3$; --;

line 29, change "-NH" to -- -NH$_2$ --;

line 31, change "F—$_2$—CFH-" to -- F$_2$-CFH- --; and change "-OCF—$_2$CF$_3$" to -- -OCF$_2$-CF$_3$ --.

Signed and Sealed this

Fourteenth Day of July, 1992

Attest:

DOUGLAS B. COMER

Attesting Officer

Acting Commissioner of Patents and Trademarks